United States Patent [19]

Aihara

[11] Patent Number: 4,699,767
[45] Date of Patent: Oct. 13, 1987

[54] LIQUID TRANSFER APPARATUS FOR AUTOMATIC ANALYZERS

[75] Inventor: Takayuki Aihara, Hachioji, Japan

[73] Assignee: Olympus Optical Company, Ltd., Japan

[21] Appl. No.: 467,788

[22] Filed: Feb. 18, 1983

[30] Foreign Application Priority Data

Feb. 24, 1982 [JP] Japan .................................. 57-28257
Feb. 24, 1982 [JP] Japan .................................. 57-28258
Mar. 19, 1982 [JP] Japan .................................. 57-42882

[51] Int. Cl.$^4$ ...................... G01N 21/13; G01N 35/04
[52] U.S. Cl. ...................................... 422/65; 141/130; 436/48
[58] Field of Search ..................................... 422/63–65, 422/67, 100; 364/497; 436/48; 141/130, 392; 198/482, 614

[56] References Cited

U.S. PATENT DOCUMENTS

| 3,475,130 | 10/1969 | Baruch | 422/64 |
| 3,751,985 | 8/1973 | Kned et al. | 436/48 X |
| 4,171,715 | 10/1979 | Forsström | 141/130 |
| 4,260,580 | 4/1981 | Sindo et al. | 422/67 |
| 4,276,051 | 6/1981 | Ginsberg et al. | 422/67 |
| 4,363,245 | 12/1982 | Schmid | 422/65 |
| 4,387,076 | 6/1983 | Cabrera et al. | 422/67 |
| 4,413,534 | 11/1983 | Tomoff et al. | 422/65 |

FOREIGN PATENT DOCUMENTS 0168555 12/1981 Japan .................................. 422/64

Primary Examiner—Barry S. Richman
Assistant Examiner—C. M. Delahunty
Attorney, Agent, or Firm—Ostrolenk, Faber, Gerb & Soffen

[57] ABSTRACT

A liquid transfer apparatus for use in an automatic analyzer successively transfers a number of liquid vessels in a continuous manner to a liquid pick up station where a probe of a liquid distributor is used to perform a liquid analysis and inserts by interruption a specified liquid vessel holding specified liquid such as an emergent test sample into the liquid pick up station when necessary to perform an analysis in an emergency by interruption during a normal operation.

15 Claims, 17 Drawing Figures

LIQUID TRANSFER APPARATUS FOR AUTOMATIC ANALYZERS

BACKGROUND OF THE INVENTION

The present invention relates to a liquid transfer apparatus for automatic analyzers, and more particularly to apparatus of this type for automatic analyzers that sequentially transfer a plurality of sample vessels holding liquid samples, such as samples to be analyzed, to a station where a probe of a liquid distributor is disposed.

In that automatic analyzer which performs the analysis of components that are contained in a test sample such as blood serum or urine, it is a common practice that after a number of liquid vessels, each containing test liquids such as samples to be analyzed, have been set on a liquid transfer apparatus these vessels are sequentially transferred to a predetermined station, the liquid samples in the vessels are picked up by means of a probe for a liquid distributor at the station and then these liquids thus picked up are transferred by the probe to another station where while analysis is performed. In the automatic analyzer which performs such sequential operations, there are instances where a predetermined analysis is being performed after a number of liquid vessels have been set in the liquid transfer apparatus there arises an urgent need to perform the analysis of another test sample or to apply various corrections by inserting the analysis of a standard sample such as a control blood serum or the like. In such cases, a conventional automatic analyzer generally conducts the analysis by removing a liquid vessel which has been set in the liquid transfer apparatus and then inserting a specified liquid vessel which contains a sample requiring testing urgently or a standard sample at the position where the liquid vessel taken out was. However, such a changing of liquid vessels is extremely troublesome and there is a case in which the order of analyzing procedures for liquid samples such as samples previously set on the liquid transfer apparatus are disturbed due to the necessity of setting the removed liquid vessel at another position of the liquid transfer apparatus. In addition, it is difficult to manually exchange and set a liquid vessel in the vicinity of a position where the liquid sample is to be picked up, where a probe and the like of a liquid distributor exist. It is conventional, therefore, that the specified liquid vessel be inserted at a position considerably upstream of a number of liquid vessels, for example ten or more, from a predetermined operation position. As a result, considerable time elapses before the analysis of the liquid sample in the specified liquid vessel is initiated and much more time is required when there are many analyzing items for liquid in each of the liquid vessels between the position where the specified liquid vessel is inserted and the predetermined operation position.

SUMMARY OF THE INVENTION

In view of the foregoing, it is an object of this invention to provide a liquid transfer apparatus for automatic analyzers which enables prompt execution of analysis procedures for a specified liquid such as a sample that requires testing immediately, which will be referred to as an urgent test sample, or standard test samples or the like, during the analysis of many liquids (i.e. sample, reagent or the like) which are placed on a liquid vessel transfer means.

In accordance with this invention, it is possible to perform the prompt analysis of a specified liquid since a specified liquid vessel holding an urgent test sample can be arbitrarily inserted whenever it is desired to do so into the path which is normally occupied by liquid vessels of routine analysis samples.

Additionally, in accordance with the invention, it is possible to increase the liquid holding vessel capacity of the automatic analyzer since additional liquid vessels can be placed at locations on the turntable where liquid vessels which hold urgent samples are sometimes mounted.

DETAILED DESCRIPTION OF THE PREFERRED EMBODIMENTS

Figure 1:
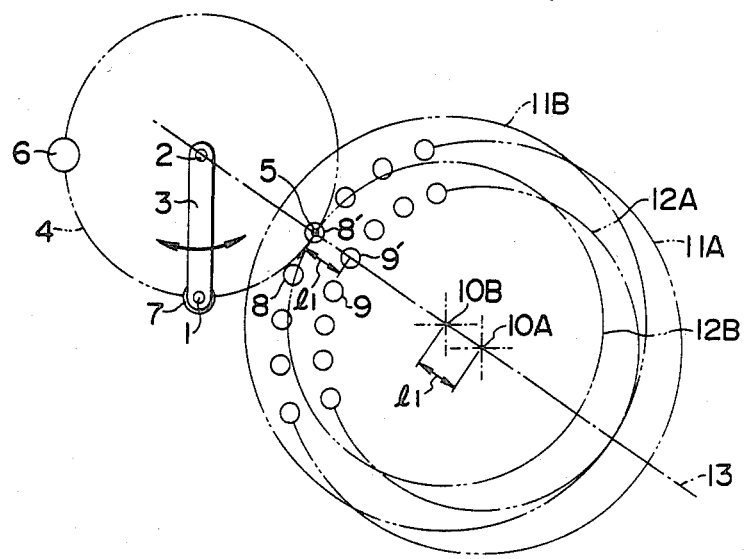
FIG. 1 is a schematic plan view that provides a visual explanation of the principle of a liquid transfer apparatus according to a first embodiment of the invention.

Referring now to FIG. 1, there is shown the relationship between a probe of a liquid distributor and liquid vessels mounted on a turntable in the form of a liquid vessel transfer means. In order to simplify the drawing of FIG. 1 the illustration of the turntable itself is omitted. In FIG. 1, the probe 1 of liquid distributor in an automatic analyzer is held at the end of an arm 3 which is rotatable around the rotation axis 2 so as to be movable, generating locus 4. The probe 1 is stoppable at each of a picking up station 5, an ejecting station 6 and a water rinsing station 7. The probe 1 at picking up station 5 picks up liquid in a liquid vessel 8 positioned at the station 5, ejects the picked up liquid into a test tube or the like at the ejecting station 6 and then is rinsed by water after returning to the rinsing station 7. Thus, a sequence of operations is completed. On the turntable, a number of liquid vessels in a plurality of lines, for example, vessels 8 and 9 in two circle lines as shown in FIG.

1, are mounted concentrically at an equidistance in each line. The turntable in its normal state has a center 10A of rotation and therefore liquid vessels 8 and 9 move along circles 11A and 12A as the turntable rotates, respectively. Under the conditions, vessels 8 on the outer circle pass through the picking up station 5 of the probe 1. The turntable is rotatable intermittently with a pitch corresponding to a distance between vessels of each circle line. Rotation of the turntable at the normal state follows that vessels 8 of the outer circle line are successively conveyed to the picking up station 5 and liquid in vessel 8 which reaches the station 5 is picked up by means of probe 1 which is rotated to the station 5.

When the successive transfer of vessels on the outer circle line to the picking up station 5 is completed or when necessary even while transferring vessels 8, the turntable can be moved by a predetermined distance $l_1$ along the center line 13 which connects the center of rotation 10A of the turntable and the rotation axis 2 of the arm 3 of the probe 1 toward the axis 2. With this movement of the turntable, its center of rotation is transferred from the position 10A to 10B which are separated by the predetermined distance $l_1$. The distance $l_1$ corresponds to the radial distance between circles 11A and 12A. Therefore, the series of vessels 8 is moved from the circle 11A to 11B and the series of inner vessels 9 is moved from the circle 12A to 12B namely to a point which coincides to the circle 11A at the picking up station 5. Thus, after the center of rotation is adjusted the inner vessels 9 pass through the picking up station 5. Namely, the intermittent rotation of the turntable causes inner vessels 9 to rotate successively to the picking up station 5 and liquid in vessel 9 at the station 5 is picked up by the probe 1.

Since the inner and outer vessels are similar, the vessel transfer capacity provided by this invention can be increased if additional liquid vessels are accommodated in the inner circle on the turntable. The size of the turntable remains constant although additional vessels are added. It is also to be noted that the switching mechanism to switch the turntable to select inner or outer vessels is simple and involves merely radial shifting of the turntable.

As described above, since the switching operation for shifting the turntable horizontally in a radial direction can be performed at any time, it is possible to conduct an emergency analysis by interruption of the normal procedure as follows. By way of example, let it be assumed that a series of outer vessels 8 are provided for holding liquid to be analyzed according to a normal routine procedure and a series of inner vessels 9 are for holding specified liquids to be analyzed in a special way. These may include emergency test samples or standard samples. The process is carried out by interrupting the routine analysis by shifting the turntable radially into the path normally occupied by vessels 8. A specified liquid vessel 9' from a series of specified liquid vessels 9 is set immediately in a place of vessel 8' at the picking up station 5. Then, the special analysis of liquid in specified liquid vessels 9 which follow the specified vessel 9' can be performed.

Figure 2:
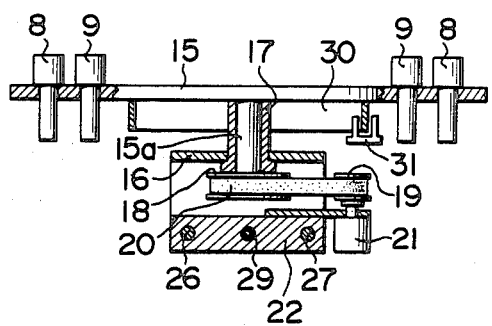
FIGS. 2 through 4 are a longitudinal section, a side and a bottom plan view, respectively, illustrating a physical embodiment of the liquid transfer apparatus in FIG. 1.
Figure 3:
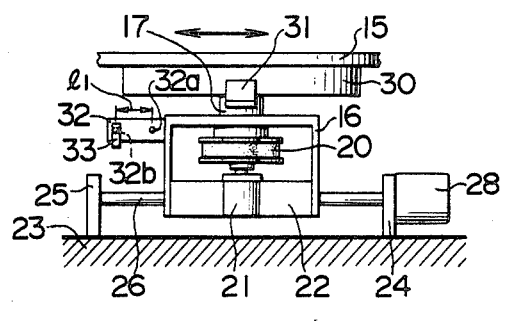
Figure 4:
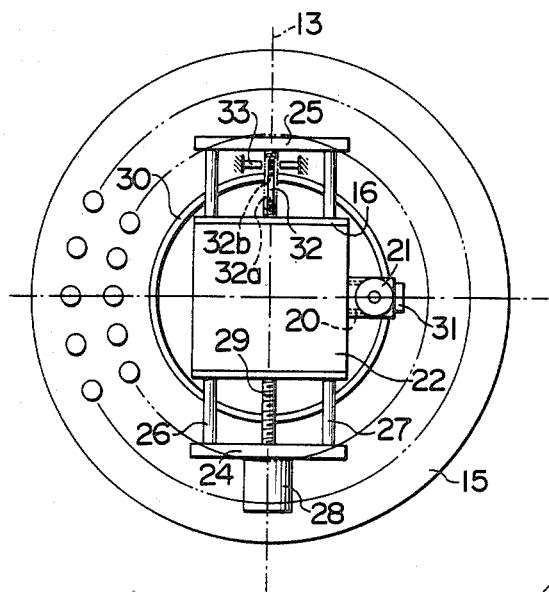

In FIGS. 2 through 4, which illustrate the structure of an actual drive mechanism for the liquid transfer apparatus, a turntable 15 on which liquid vessels 8 and 9 are mounted is supported in a rotatable manner by a bearing 17 which is secured to a bracket 16 so that the drive force of motor 21 is transmitted to a rotary shaft 15a of turntable 15 through a reduction mechanism comprising pulleys 18 and 19 and belt 20. The bracket 16 is secured to a slider 22 which is slidably mounted on slide shafts 26 and 27 disposed in parallel between supporting plates 24 and 25 which are secured to a stationary base 23. A slide mechanism is constructed so as to be rotatable by means of motor 28 attached to supporting plate 24 in such a manner that a slide screw 29 which is disposed in parallel with slide shafts 26 and 27 is threadably engaged with slider 22. Consequently, during rotation of motor 28 bracket 16 may be moved along the center line 13 connecting the center of rotation 10A of the turntable to rotation aixs 2 of arm 3 of probe 1, as described above with reference to FIG. 1, under guidance of slide shafts 26 and 27.

In addition, to detect a reference position with regard to rotation of turntable 15, a sensor 31 is provided which comprises a reference marker for rotation (not shown) such as a hole formed on a ring member 30 which is disposed at the back of turntable 15 concentrically with rotary shaft 15a and a photocoupler disposed on a grasping ring member 30.

The displacement distance of the turntable in the radial direction is detected by the cooperation of a plate member 32 having markers 32a and 32b such as two holes which is secured to bracket 16 and a sensor 33 such as a photocoupler which cooperates with grasping plate member 32. The distance between the two markers 32a and 32b equals the displacement $l_1$ of the center of rotation of the turntable as illustrated in FIG. 1.

With the liquid transfer apparatus arrangement as described above, the transfer of liquid such as a test sample from the picking up station 5 by means of probe 1 of the liquid distributor shown in FIG. 1 is initiated by a command signal from a control apparatus (not shown) operating with a predetermined program. In other words, when the liquid transfer apparatus is initiated to operate in the normal way the turntable 15 is intermittently rotated by means of motor 21 where the center of rotary shaft 15a is at the position 10a. At this time, marker 32a faces sensor 33 and liquid vessels 8 in the outer circle on turntable 15 are successively transferred to the picking up station 5. Completion of the liquid transfer operation of outer vessels 8 to the picking up station 5 is detected by sensor 31 and causes motor 28 to rotate in response to the detected signal and thus turntable 15 is moved along slide shafts 26 and 27 toward rotation axis 2 of arm 3 of probe 1 together with slider 22. The position where sensor 33 faces marker 32b is detected by means of sensor 33 and in turn motor 28 is stopped in response to the detected signal. At this time, the center of rotation axis 15a of turntable 15 is at the position 10B and inner vessels 9 are on the circle 12B passing through the picking up station 5.

Thus, after rotary shaft 15a reaches the rotation center 10B by moving turntable 15 toward pivot axis 2 of probe 1, turntable 15 is rotated intermittently as described above and inner vessels 9 are successively transferred to the picking up station 5 as was the case for outer vessels 8. With the construction described above a large number of liquid vessels can be mounted by arranging them concentrically within each other even though turntable 15 has a small diameter. The picking up station 5 of probe 1 of the liquid distributor can be fixed at one position while at the same time any of the vessels can be reached.

The motor 28 in the sliding mechanism for shifting rotary shaft 15a of turntable 15 from the position 10A to 10B may also be initiated by means of an interrupting switch (not shown). When turntable 15 is shifted by the sliding mechanism through operation of such interrupting switch, the liquid transfer operation of liquid vessels 8 is interrupted even while outer vessels 8 are successively transferred to the picking up station 5 and an inner liquid vessel 9' radially aligned with vessel 8' lying at the station 5 prior to the interruption is moved to the station 5. Thus, when inner vessels 9 are used for specified liquid vessels holding specified liquids to be analyzed by insertion on the way of normal operation, it is possible to transfer specified liquid vessels 9 to the picking up station 5 at any time during the transfer of liquid vessels 8 holding liquids to be analyzed in the normal operation.

It is also to be noted that the order of transferring liquid is not limited specifically to the order described above. By way of example, outer vessels 8 and inner vessels 9 on turntable 15 may be transferred alternately and it is also possible to produce other orders of vessel transfer.

As described above vessels 8 and 9 are arranged concentrically on the turntable 15 as shown. It is to be understood, however, that liquid vessels may be arranged in a plurality of more than two circle lines and also there is no necessity for arranging liquid vessel lines radially. By way of example, liquid vessels may be arranged spirally. In this case, the center of turntable 15 may be shifted little by little along the center line 13 simultaneously with rotation of turntable 15.

Figure 5:
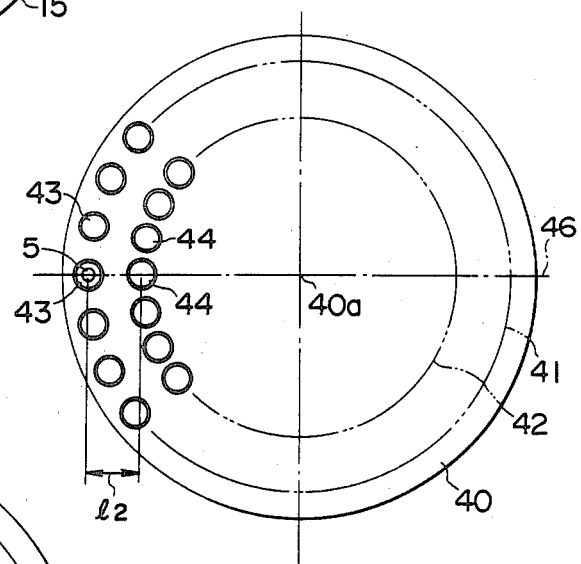
FIGS. 5 and 6 are schematic plan views illustrating conditions before and after the inserting operation in a liquid transfer apparatus illustrating a second embodiment of the invention, respectively.
Figure 6:
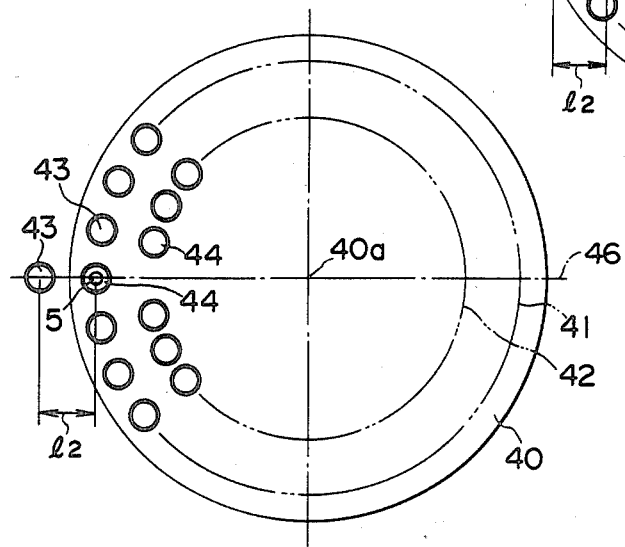

FIGS. 5 and 6 are provided for describing the operation of a liquid transfer apparatus according to a second embodiment of the invention and illustrate the positional relation between a picking up station of a probe of a liquid distributor and liquid vessels mounted on a turntable in the form of a liquid vessel transfer means. In FIG. 5, a number of liquid vessels 43 and equal number of liquid vessels 44 are mounted on turntable 40 with a center 40a at an equal pitch and in two circles 41 and 42 with the same center 40a which have different radii, respectively. A required number of liquid vessels are mounted through the circumference of two circles 41 and 42 similar to the first embodiment. Only part of these vessels are shown in FIGS. 5 and 6 for simplification. A picking up station as shown in FIG. 1 is provided at a fixed position in the outer circle 41 on turntable 40, which is shown in FIGS. 5 and 6 with reference numeral 5. When turntable 40 is rotated intermittently, liquid vessels 43 in outer circle 41 are successively transferred to the picking up station 5, at which liquid held in liquid vessels 43 is picked up by means of a probe.

When the liquid vessels 44 on the inner circle 42 are transferred successively to a point opposite to the picking up station 5 under the normal mode of operation shown in FIG. 5, vessels 44 which move on the circumference of circle 42 as turntable 40 turns intermittently are therefore not transferred to the picking up station 5 itself.

Accordingly, in the second embodiment, outer and inner vessels 43 and 44 form pairs comprising one outer vessel and one inner vessel which are aligned at the same rotation angle, each pair being movable outwardly of turntable 40 in the radial direction. The distance through which a pair of vessels 43 and 44 is movable radially relative to turntable 40 corresponds to the distance $l_2$ between a pair of vessels 43 and 44. Thus, in this liquid transfer apparatus, outer vessels 43 are successively transferred to the picking up station 5 as turntable 40 turns intermittently as described above. As for inner vessels 44 as shown in FIG. 6, one inner vessel 44 to be inserted for the analysis is shifted outwardly with respect to the rotary axis 40a of turntable 40, when the vessel 44 reaches the picking up station 5 and then is transferred to the picking up station 5. At this time, the outer vessel 43 paired with the inner vessel 44 transferred to the picking up station 5 is projected outwardly from turntable 40.

The order of transferring inner vessels 44 to the picking up station 5 may be selected to be conducted after outer vessels 43 have completed one revolution of turntable 40 or to follow immediately its paired outer vessel 43 after each intermittent rotation of turntable 40. Also in this liquid transfer apparatus, since two lines of liquid vessels are arranged on turntable 40 in the same manner as in the first embodiment, the liquid transfer capacity can be increased without increasing the size of altering the shape of the turntable. As in the first embodiment, inner vessels can be transferred to the picking up station 5 by shifting only an inner vessel in the radial direction of a turntable, the picking up station 5 remaining stationary. In addition, when the necessity of conducting an analysis of specified liquid such as an emergency test sample or a standard sample occurs, it is possible to conduct the analysis of the specified liquid by interrupting the normal sequence. By way of example, outer vessels 43 are successively transferred to the picking up station 5 during the normal operation and when the necessity of an analysis for specified liquid such as an emergency test sample or a standard sample occurs during the transfer of outer vessels in the normal operation inner specified vessels 44 holding specified liquid are mounted on inner circle 42 and then are shifted to the picking up station 5 when the inner specified vessels 44 reach the location of the station 5.

Figure 7:
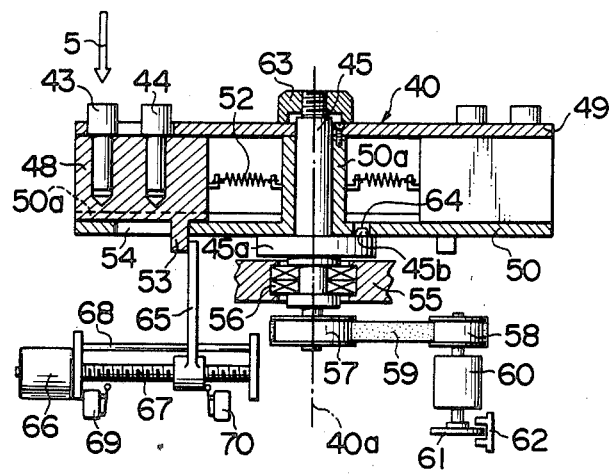
FIG. 7 is a longitudinal section view illustrating a physical embodiment of the liquid transfer apparatus in FIG. 5.

Referring now to FIG. 7, which illustrates a construction of a drive mechanism of the liquid transfer apparatus of FIGS. 5 and 6, two liquid vessels 43 and 44 which are disposed in radial alignment on turntable 40 are held on the same vessel holder 48. Similarly, other liquid vessels in axial alignment on turntable 40 form respective pairs of an outer and inner vessel, 43 and 44 respectively, in radial alignment, each couple being held on respective independent vessel holders. Since the construction of these vessel holders is the same, only vessel holder 48 shown in FIG. 7 will be described. Turntable 40 comprises an upper plate 49, a bottom plate 50 and a number of vessel holders 48 which are constructed in a radial manner to hold a pair of liquid vessels 43 and 44 in radial alignment. The vessel holder 48 is interposed between upper plate 49 and bottom plate 40 and is movable in the radial direction of turntable 40 along a rail 50b provided on bottom plate 50. Additionally, the vessel holder 48 is always biased toward a rotary shaft 45 by means of the resilience of a coil spring 52 which is interposed under tension between the holder 48 and a cylindrical portion 50a integral with bottom plate 50 so that outer vessels 43 are on circle 41 in the normal condition and can pass through the picking up station 5 of probe 1 as turntable 40 turns.

A projection 53 is further provided on the lower part of vessel holder 48. The projection 53 protrudes downwardly through a longitudinal hole 54 which is formed on bottom plate 50 of turntable 40 in the radial direction of the latter. Consequently, when the projection 53 is moved outwardly of turntable 40 along longitudinal hole 54, the vessel holder 48 is moved against the pull of the spring 52 so that inner vessels 44 which are held on vessel holder 48 on the circle 42 can be shifted to the position on the circle 41, namely to the picking up station 5 of probe 1.

The rotary drive shaft 45 of turntable 40 is held by a bearing 56 fixed to a body base plate 55 and rotation of a motor 60 is transmitted thereto through a reduction mechanism including pulleys 57 and 58 and a belt 59. A disc 61 having a rotation reference marker is fixed on a rotation shaft of motor 61. The rotation reference positions and rotational cycles of turntable 40 are detected by means of disc 61 and a sensor 62 which is secured to a stationary member. The rotary drive shaft 45 has a base portion 45a with a larger diameter so as to mount turntable 40 on the base portion 45a. The turntable 40 is removably attached to drive shaft 45. The removal of turntable 40 from drive shaft 45 is effected by removing a fixing nut 63 threadably engaged to drive shaft 45 at the center of turntable 40 and by pulling turntable 40 upwardly. The mounting of turntable 40 is effected by threadably mounting it to drive shaft 45 with fixing nut 63 after positioning a protruded pin 45b which is provided on base portion 45a of drive shaft 45 in place by inserting the pin 45b into a positioning hole 64 provided in bottom plate 50 of turntable 40.

When turntable 40 is turned to transfer outer vessels 43 to the picking up station 5, a protrusion 53 provided on the lower part of vessel holder 48 holding liquid vessels 43 engages with a transfer arm 65 which is provided below turntable 40. The arm 65 engages threadably with a feed screw 67 which is driven by a reversible motor 66 to move along a guide bar 68 in the radial direction of turntable 40. The normal rotational direction of motor 66 causes the arm 65 to bear against the protrusion 53 so as to pull out vessel holder 48 outwardly of turntable 40. When inner vessel 44 mounted on vessel holder 48 reaches a position facing the picking up station 5, the arm 65 is brought into engagement with and thereby operates a limit switch 69 to stop motor 66. At this time, outer vessel 43 which is at the picking up station 5 is now shifted outwardly of turntable 40 and inner vessel 44 takes the place of outer vessel 43 at the picking up station 5. When the transfer arm 65 is moved toward the center axis 40a of turntable 40 (by driving the motor 66 in reverse), upon picking up liquid in inner vessel 44 by the probe, movement of the vessel holder 48 follows the arm 65 under the resilience force of coil spring 52. When the arm 65 abuts and thereby operates a limit switch 70, the motor 66 stops at a position corresponding to the position the vessel holder 48 occupied previously.

In the liquid transfer apparatus described just above, the transfer of liquid vessels 43 and 44 to the picking up station 5 is conducted by command signals from a control device (not shown). Under normal conditions, the turntable 40 is intermittently turned by driving the motor 60 in response to command signals from the control device to successively transfer outer liquid vessels 43 on the turntable 40 to the picking up station 5. On the other hand, it is possible to provide another operating mode as follows. The starting point of rotation of the second round for turntable 40 is detected, for example, by counting signals from the sensor 62 by means of the control device, and thereby the turntable 40 is caused to rotate intermittently and each vessel holder 48 is successively shifted outwardly of the turntable 40 by means of the arm 65 by driving the reversible motor 66 in the normal rotation direction whenever the turntable 40 is interrupted to rotate starting from the second revolution of turntable 40. Thus liquid vessels 44 in the inner circle 42 on the turntable are shifted to be on the outer circle 41 and thus are transferred to the picking up station 5. At this time the limit switch 69 is actuated by the arm 65 to stop the motor 66 and in turn the probe is lowered at the picking up station 5 to pick up a required amount of liquid from vessels 44. Thereafter, rotation of the motor 66 is reversed by a command signal from the control device and the arm 65 is moved to actuate the limit switch 70. Upon actuation of the switch 70, vessel holder 48 returns to the original position by action of the coil spring 52 and the motor 66 ceases to rotate. When such operation is repeated with regard to each of vessel holders 48 whenever it reaches a predetermined position on the center line 46 connecting the picking up station 5 and the center axis 40a of turntable 40 as the latter rotates, liquid vessels 44 in the inner circle 42 on the turntable 40 can be successively transferred to the picking up station 5.

As stated above, the order of transferring liquid vessels 44 to the picking up station 5 is not limited specifically as described above. By way of example, the liquid transfer may be carried out by repeating the operation which causes inner vessel 44 to be transferred after the use each outer vessel 43. Further, three or more liquid vessels may be arranged one each vessel holder 48.

Since inner vessels 44 can be selectively transferred to the picking up station 5 of the liquid distributor, the places where inner vessels are mounted on the vessel holders may be conveniently used for inserting specified liquid vessels holding specified samples into the picking up station 5 by interrupting the normal analysis, when necessary in cases such as analysis of emergency test samples. At this time, the specified liquid vessel 44 which follows a given liquid vessel 43 which is normally handled is shifted outwardly of the turntable 40 and is transferred to the picking up station 5 to carry out an emergency analysis.

Figure 8:
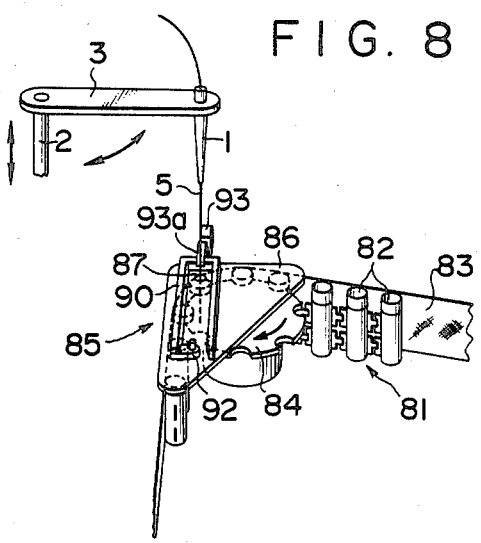
FIG. 8 is a perspective view of the essential parts of a liquid transfer apparatus constructed in accordance with a third embodiment of the invention.
Figure 9:
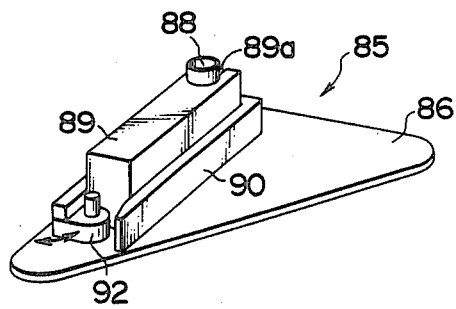
FIGS. 9 and 10 are a perspective and a longitudinal section, respectively, of a mechanism for holding specified liquid vessels shown in FIG. 8.
Figure 10:
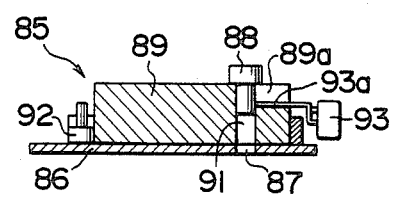

Illustrated in FIG. 8, is a liquid transfer apparatus according to a third embodiment of the invention, which uses a snake chain system as a liquid vessel transfer mechanism. The liquid vessel transfer mechanism 81 is to drive a snake chain 83 holding liquid vessels 82 by means of a sprocket ring 84. Liquid vessels 82 which are held by snake chain 83 are successively transferred to a predetermined picking up station 5 as sprocket ring 84 is rotated intermittently. At the station 5, liquid stored within vessel 82 is withdrawn by a probe 1 which is rotatably supported and vertically movable. A mechanism 85 for holding specified liquid vessels is disposed over the liquid vessel transfer mechanism 81 at the station 5. The holding mechanism 85 includes a base 86 which is secured to a stationary member. The base 86 has a through-hole 87 through which probe 1 goes into liquid vessel 82 which is held on snake chain 83 even when holding mechanism 85 is at the station. The base 86 also includes a guide 90 for positioning a rack 89 which holds a specified liquid vessel 88 holding liquid to be adventitiously analyzed such as an emergency test sample or a standard sample, as shown in FIGS. 9 and 10. When rack 89 is mounted on base 86 by positioning rack 89 by means of guide 90, as shown in FIG. 10, a through-hole 87 formed in base 86 and a through-hole 91 for holding a specified liquid vessel 88 are brought in alignment. Consequently, when rack 89 holding specified liquid vessel 88 is mounted on base 86, the vessel 88 is positioned at the picking up station 5. In order to position rack 89 securely and stably in place by means of guide 90, a rack fixture 92 is provided on base 86 so that rack 89 is always depressed against guide 90. To detect whether rack 89 is mounted on base 86, a rack detection switch (not shown) is provided on a rack mounting portion of base 86 and a switch 93 for detecting whether specified liquid vessel 88 is set on rack 89 which is mounted on base 90 is provided on a stationary member. An operation piece 93a of switch 93 extends through a notch 89a formed on rack 89 so as to bear against specified liquid vessel 88.

With the liquid transfer apparatus described just above, a number of liquid vessels 82 which are held on snake chain 83 are conveyed with the drive of sprocket ring 84 and probe 1 goes through through-hole 87 formed in base 86 into liquid vessel 82 at the picking up station 5 to pick up liquid therein. Whenever a specified liquid such as an emergency test sample is to be adventitiously analyzed during an otherwise routine operation, first, an emergency switch on an operation control panel (not shown) is depressed to bring the system to a standby mode upon completion of the current liquid distribution mode of operation. The standby mode is detected conventionally such as by an operation control panel or an analyzer. Next, the rack 89 which holds the specified liquid vessel 88 which is to be positioned out of sequence is set on base 86 to position the vessel 88 at the picking up station 5. Based on a signal from a rack detection switch (not shown) for detecting the setting of rack 89, the probe 1 descends at the station 5 to pick up liquid stored within the specified liquid vessel 88. The vertical displacement of probe 1 into the vessel 88 can be fixed to a predetermined value or the position of the probe 1 can be controlled by the liquid level in the vessel. When specified liquid 88 is not held on rack 89 which is mounted on base 86, an alarm signal from switch 93 and probe 1 of the liquid distributor can bring the system into an inoperative condition. Upon completion of the handling of the specified liquid, rack 89 is removed from base 86 and a start switch for the normal routine operation which is provided on the operation control panel is operated to resume the normal routine operation for transferring liquid vessels 82 to the station 5 by means of snake chain 83. Thus, according to this embodiment, it is possible to analyze specified liquid promptly since specified liquid vessel 88 holding an emergency test sample can be inserted during the normal routine distributing operation after a predetermined distributing operation is conducted with regard to liquid vessel 82 which is held on snake chain 83 at the station 5. Additionally, specified vessel 88 is removably mounted on base 86 together with rack 89 in this embodiment. Therefore, specified liquid vessel 88 is typically removably secured by fixing base 86 to rack 89. In the case where a plurality of specified liquid vessels 88 are to be analyzed, after inputting the number of vessels to be handled out of sequence into the operation control panel, an emergency operation can be conducted by successively replacing specified liquid vessels 88 or by alternating operations of the switch for emergency and setting of specified vessel 88 each time for every specified vessel.

Figure 11:
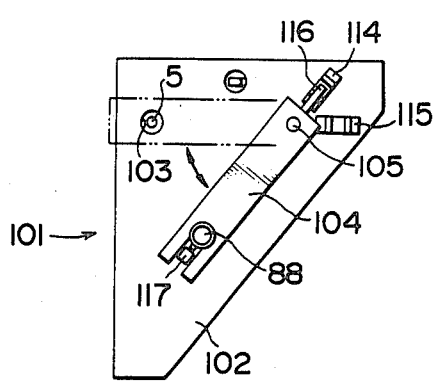
FIGS. 11 and 12 are a plan view and a front view, respectively, of another mechanism for holding specified liquid vessels.
Figure 12:
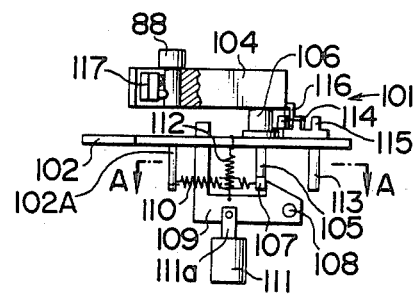
Figure 13:
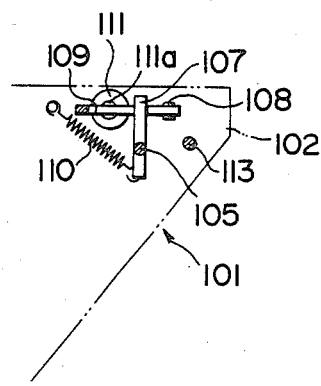
FIG. 13 is a section view taken along the line A—A in FIG. 12 looking in the direction of arrows A—A.

In FIGS. 11 through 13, which illustrate another embodiment of a mechanism for holding specified liquid vessels. The holding mechanism 101 transfers specified liquid vessels 88 which are set at another position, to the station 5 by operating a switch for emergency on an operation control panel. A base 102, similar to that of the embodiment in FIG. 8, is fixed to a stationary member over a liquid vessel transfer mechanism 81 and is provided with a through-hole 103 through which probe 1 passes at a position corresponding to the picking up station 5. A rack 104 which holds specified vessel 88 at one end thereof is rotatably supported by a shaft 105 which is secured to rack 104 passing through base 102, through a bearing 106 at the other end thereof. Rotation of rack 104 causes specified liquid vessel 88 which is held on rack 104 to be either aligned with the position of through-hole 103 and the picking up station 5 or to be in a stand by position kept away from the latter. Under the lower surface of base 102, an arm 107 which is secured to shaft 105 is prevented from turning by a protrusion located on a lever 109 on one end, the lever being rotatably mounted around a shaft 108. A tension spring 110 is attached between a protrusion 102A from the lower surface of base 102 and arm 107. Consequently, rack 104 is biased clockwise, turning its end which holds specified liquid vessel 88 toward the picking up station 5. A plunger 111a of solenoid 111 is secured to lever 109 and a tension spring 112 is provided between base 102 and lever 109. During deenergization of solenoid 111 rack 104 is prevented from turning under the force of tension spring 110 since one end of arm 107 is caught by the lever 109. During energization of solenoid 111 lever 109 is pulled downwardly (see FIG. 12) against the force of spring 112 and thus it releases its hold on arm 107 and rack 104 is turned clockwise by the force of spring 110. A stopper 113 engages the arm 107. The stopper 113 is located on the lower surface of base 102 in such a manner that specified liquid vessel 88 which is held on rack 104 is positioned at the station 5 when arm 107 turning under the force of spring 110 engages stopper 113. Two sensors 114 and 115 are provided on the upper surface of base 102 to detect a rotational position of rack 104. When rack 104 is in its position shown by the solid line in FIG. 11, this position is detected because a screen 116 provided on rack 104 cooperates with sensor 114. When rack 104 is at the position corresponding to the picking up station 5, as shown in phantom in FIG. 11, the position is detected by action of sensor 115. Rack 104 is further provided with a switch 117 for detecting whether specified liquid vessel 88 is mounted on rack 104, similar to the embodiment shown in FIG. 8.

With the embodiment described just above, rack 104 is at a stand by position as shown in FIG. 11 with a solid line during the normal operation since solenoid 111 is in a deenergized condition and probe 1 of the liquid distributor enters liquid vessel 82 held on snake chain 83 (FIG. 8) through hole 103 formed in base 102 at the station 5 to pick up liquid. Thus the distributing operation is conducted. When the necessity of conducting an emergency analysis such as an emergency test sample occurs during the normal operation, specified liquid vessel 88 holding liquid to be analyzed in an emergency is set on rack 104 and immediately after the distributing operation of liquid presently being conducted is completed, by depressing a switch for emergency on the operation control panel (not shown), the operation for emergency is initiated with solenoid 111 being energized. Engagement between arm 107 and lever 109 is released by energization of solenoid 111 and rack 104 is rotated by spring 110 until arm 107 bears against stopper 113 to position specified liquid vessel 88 at the picking up station 5. Under this condition, probe 1 enters specified liquid vessel 88 to pick up liquid and thus the distributing operation is conducted. When specified liquid vessel 88 is not set on rack 104, a warning is given by switch 117 and solenoid 111 is brought into an inoperative condition so as not to rotate rack 104 toward the station 5. Solenoid 111 is deenergized in synchronism with completion of the distributing operation of specified liquid vessel 88 and rack 104 is returned manually against the force of spring 110 to the standby position to engage arm 107 with lever 109. The return of rack 104 to the standby position may be conducted automatically using a well known motor drive or belt drive.

Figure 14:
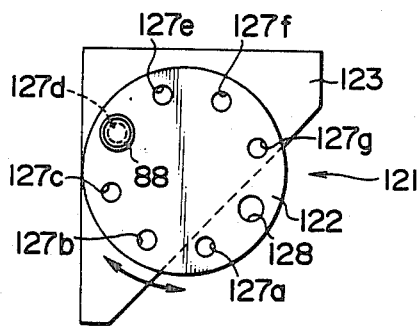
FIGS. 14 and 15 are a plan view and a longitudinal section respectively of a further mechanism for holding specified liquid vessels.
Figure 15:
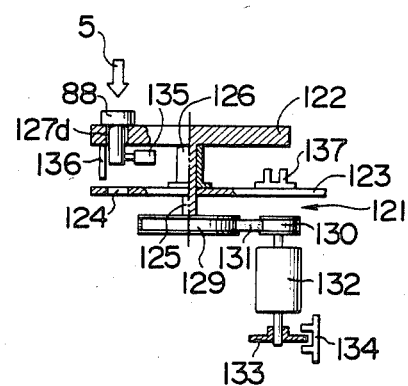

In FIGS. 14 and 15, which illustrate a further embodiment of the specified liquid vessel holding mechanism, the holding mechanism 121 is provided so as to set specified liquid vessel 88 on a holding body 122 of the turntable type. A base 123 is secured to a stationary member over the liquid vessel transfer mechanism 81 similar to the embodiment shown in FIG. 8 and is provided with a through-hole 124 through which probe 1 passes at a position corresponding to the picking up station 5. Base 123 is provided with a rotary shaft 125 connected to holding body 122 which is rotatably held on base 123 such that the shaft 125 is supported by a bearing 126 which is fixed on base 123. The holding body 122 is provided along a circular periphery thereof with vessel holding portions 127a through 127g for removably holding a plurality of specified liquid vessels 88. A through-hole 128 through which probe 1 of the liquid distributor passes is also provided on body 122, on the same circular periphery as vessel holding portions 127a through 127g and through-hole 128 can be aligned with the position of through-hole 124 as holding body 122 turns. The rotary shaft 125 which extends under base 123 is connected to an output shaft of a motor 132 through a reduction gear including pulleys 129 and 130 and a timing belt 131. A rotary plate member 133 which has a rotation reference marker is secured to the output shaft of motor 132. By detecting rotation of rotary plate member 133 by means of sensor 134 which is fixed on a stationary member, it is possible to detect a rotational position where one of vessel holding portions 127a through 127g is in alignment with through-hole 124 of base 123. A switch 135 for detecting whether specified liquid vessel 88 is present on holding body 122 is provided adjacent to the picking up station 5 on a stationary member. Rotary holding body 122 is further provided with a projection 136 for a screen which protrudes toward base 123 and a sensor 137 for detecting projection 136 is provided on base 123 so that the position where through-hole 128 of rotary holding body 122 is in alignment with through-hole 124 of base 123 can be detected. The projection 136 is located at a predetermined angular location on body 122.

With the embodiment described just above, projection 136 of holding body 122 is detected by sensor 137 during the normal operation so that through-hole 128 comes into alignment with through-hole 124 and probe 1 of the liquid distributor enters liquid vessel 82 which is held on liquid vessel transfer mechanism 81 through through-holes 128 and 124 which are in alignment with each other at the picking up station 5 to conduct the distributing operation of a liquid. When the necessity of conducting analysis of a plurality of specified liquids such as emergency test samples occurs during the normal operation, a plurality of specified liquid vessels 88 holding these liquids are set at any positions of vessel holding portions 127a through 127g and then a switch for emergency operation of the control panel (not shown) is depressed. As a result, motor 132 is driven in synchronism with the completion of the distributing operation for the liquid vessel 82 which is held on liquid vessel transfer mechanism 81 at the picking up station 5 to rotate rotary holding body 122. With rotation of rotary holding body 122, specified liquid vessels 88 which are held on rotary holding body 122 are successively transferred to the picking up station 5 in response to output signals from sensor 134 and switch 135 to be positioned in place and liquid within specified liquid vessel 88 is picked up for the distribution. When all liquids within specified liquid vessels 88 which are set on rotary holding body 122 have been successively transferred to the picking up station 5 and the distributing operation of the liquids within specified liquid vessels is completed, sensor 137 detects projection 136 which is provided on rotary holding body 122 and thereby rotation of rotary holding body 122 is stopped at the detected position. As a result, the picking up position 5 is an alignment with through-hole 128 and thus the normal operation is resumed. According to this embodiment, similar to the first embodiment shown in FIGS. 1 through 4 and the second embodiment shown in FIGS. 5 through 7, a plurality of specified sample vessels can be advantageously set at a time.

Mechanisms 85, 101 and 121 for holding specified liquid vessels are not limited to the construction in combination with liquid vessel transfer mechanism 81 of the snake chain type. By way of example, these mechanisms can be effectively applied to the turntable system which transfers a number of liquid vessels arranged on the same circle of a turntable to a picking up station and the rack system in which a plurality of racks, each holding a number of liquid vessels, are housed within a rack cassette and after these racks are successively transferred into a predetermined transfer path a plurality of liquid vessels held within the rack are successively positioned at a picking up station.

Figure 16:
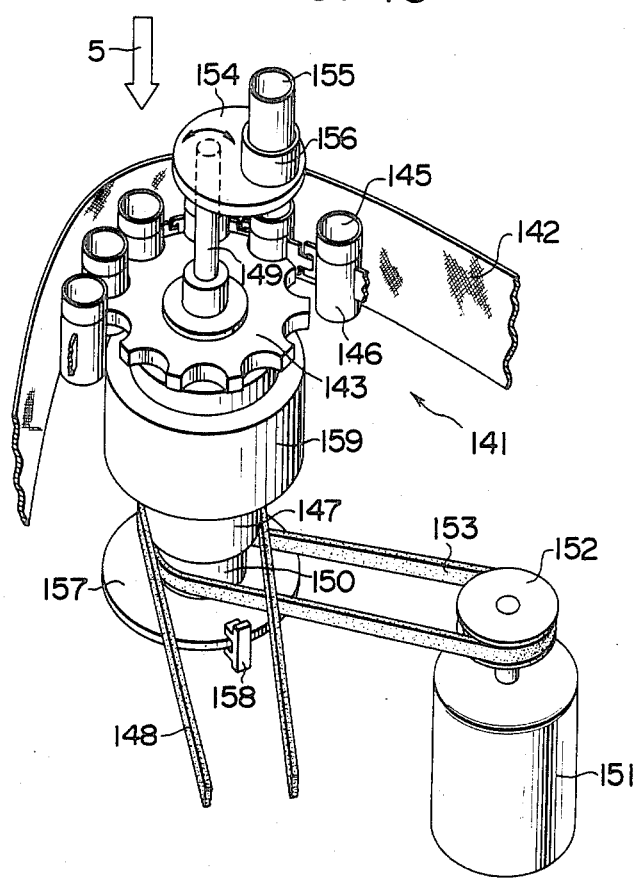
FIG. 16 is a perspective view of the essential parts of a liquid transfer apparatus illustrating a fourth embodiment of the invention.

FIG. 16 illustrates a fourth embodiment of the liquid transfer apparatus. A specified liquid vessel supporting member 154 for emergency use in the shape of a disc is disposed so as to pivot on the rotational axis 149. A sprocket ring 143 for driving snake chain 142 of the liquid vessel transfer mechanism 141 is also rotatable about the same rotational axis 149. Sprocket ring 143 drives snake chain 142 which is constructed by connecting holding portions 146 for holding liquid vessels 145 and a drive force provided by a motor (not shown) is transmitted to sprocket ring 143 through a pulley 147, which is integral with sprocket ring 143, and a timing belt 148. Shaft 149 is provided on sprocket ring 143 at the center thereof so as to be rotatable in relation to sprocket ring 143 and extends downwardly passing through the upper part of sprocket ring 143 and a stationary member 159. Pulley 150 is secured to the lower end of rotary shaft 149 and timing belt 153 is stretched between pulley 150 and pulley 152 which is integral with an output shaft of motor 151 to transmit rotation of motor 151. Small disc member 154 for holding specified liquid vessels is eccentrically secured to the upper end of rotary shaft 149. A holding portion 156 for holding one specified liquid vessel 155 is provided on holding member 154. The distance between the center of holding portion 156 and the center of rotation of holding member 154 is equal to the distance between the center of rotation of holding member 154 and the picking up position 5. A rotary plate member 157 having a rotation reference marker is secured to pulley 150 so as to rotate with rotary shaft 149 to detect a rotational position of rotary plate member 157 by means of sensor 158 provided on a stationary member.

With the liquid transfer apparatus described just above, during normal operation member 154 for holding specified liquid vessels remains at a fixed angular position where holding portion 156 for holding specified liquid vessels 155 is kept away from the picking up station 5 so that the distributing operation of liquid within liquid vessels 145 by means of probe 1 is not prevented as vessels 145 are transferred to the station 5 by means of snake chain 142. When the necessity of conducting an emergency analysis of specified liquid, such as an emergency test sample occurs during the normal operation in which liquid vessels 145 are successively transferred to station 5 and distributing operation of liquid within liquid vessels 145 is conducted, specified liquid vessel 155 holding specified liquid is set on holding portion 156 of holding member 154. Thereafter a switch for emergency (not shown) is depressed so that immediately after the distributing operation of liquid within vessels 145 on snake chain 142 at the picking up station 5 is completed, supporting member 154 which is integral with rotary shaft 149 in an eccentric condition is rotated substantially half a revolution by motor 151 to being specified liquid vessel 155 to the station 5. Arrival of specified liquid vessel 155 at station 5 is detected by sensor 158, an output of which controls stopping of motor 151. When probe 1 enters specified liquid vessel 155 to pick up liquid and the distributing operation of the liquid is completed, motor 151 resumes its rotation to rotate holding member 154 to stop at the position where specified liquid vessel 155 is kept away from the station 5. Subsequently, snake chain 142 is driven to initiate the transfer of the next liquid vessel 145 to station 5 and the normal operation is resumed. According to the liquid transfer apparatus of the embodiment of FIG. 16 described above, the construction of means for inserting specified liquid vessel 155 into the station 5 can be made compact and the operation for insertion can be conducted in a short time.

Figure 17:
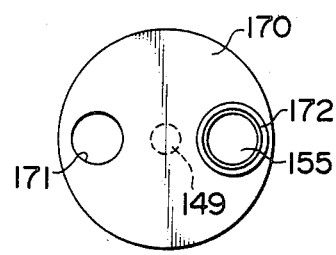
FIG. 17 is a plan view of a still further mechanism for holding specified liquid vessels in the liquid transfer apparatus shown in FIG. 16.

FIG. 17 illustrates another member 170 for holding specified liquid vessel for use instead of holding member 154 for specified liquid vessel 155. The holding member 170 is formed in the shape of a disc secured at its center to the upper end of rotary shaft 149 on which sprocket ring 143 is rotatably mounted. The holding member 170 is provided with a through-hole 171 and a holding portion 172 for holding one specified liquid vessel 155. Hole 171 and holding portion 172 are positioned in symmetrical relationship about the center of holding member 170, respectively. The distances from the rotation center of holding member 170 to the center of through-hole 171 and to the center of holding portion 172 are equal to the distance between the rotation center of holding member 170 and the station 5.

Consequently, with the liquid transfer apparatus using the holding member 170, the member 170 stays during the normal operation at the rotational angle position where through-hole 171 is in alignment with the station 5 and thus the distributing operation of liquid within liquid the vessel 145 which is transferred to the station 5 by means of snake chain 142 is conducted smoothly through through-hole 171. When specified liquid such as an emergency test sample is to be inserted during the normal operation, specified liquid vessel 155 holding specified liquid is set on holding portion 172 of holding member 170 and an emergency switch is depressed. As a result, immediately after the distributing operation of liquid within liquid vessel 145 at the station 5 is completed, holding member 170 is rotated substantially through 180° together with rotation shaft 149 by means of motor 151 to bring specified liquid vessel 155 to the station 5. Thereupon, the probe 1 enters specified liquid vessel 155 to pick up specified liquid and thus the distributing operation of the liquid is conducted. Upon completion of the distributing operation, holding member 170 is rotated substantially through 180° to move portion 172 holding specified liquid vessel 155 away from the station 5 and move through-hole 171 to the liquid picking up station 5.

What is claimed is:

1. A liquid transfer apparatus for use in an automatic analyzer comprising:

vessel conveying means for successively conveying a plurality of liquid containing vessels for routine analysis to a liquid pick up station of a liquid distributor in a predetermined sequence, said vessel conveying means including a snake chain and a motor which are disposed and constructed to intermittently move said snake chain by means of the drive force of said motor, said snake chain including means for mounting a plurality of liquid containing vessels on said snake chain with equal spacing between such a plurality of liquid containing vessels;

a liquid distributor having said liquid pick up station positioned to sequentially receive a plurality of liquid containing vessels conveyed by said vessel conveying means, a sample taking probe having one end insertable into that one of a plurality of liquid containing vessels being conveyed by said vessel conveying means which is located at said liquid pick up station for removing a sample of liquid from that one of a plurality of liquid containing vessels;

supplemental vessel conveying means supported in superimposed position by said vessel conveying means for conveying a vessel having an emergency or standard sample therein to said sample taking probe, said supplemental vessel conveying means having one position for holding a vessel conveyed by said supplemental conveying means at said liquid pick up station so that the predetermined sequence of conveying a plurality of liquid containing vessels by said vessel conveying means is interrupted so that said one end of said sample taking probe is insertable into a vessel conveyed by said supplemental conveying means instead of into that one of a plurality of liquid containing vessels conveyed by said conveying means which is located at said liquid pick up station, and at least one other position for holding a vessel conveyed by said supplemental vessel conveying means away from said liquid pick up station;

means for selectively moving said supplemental vessel conveying means between said one position and said at least one other position;

said one end of said probe being in essentially the same horizontal location when removing a sample from a vessel conveyed by said supplemental vessel conveying means as when removing a sample from a liquid containing vessel conveyed by said vessel conveying means.

2. A liquid transfer apparatus for use in an automatic analyzer comprising:

vessel conveying means for successively conveying a plurality of liquid containing vessels for routine analysis to a liquid pick up station of a liquid distributor in a predetermined sequence;

a liquid distributor having said liquid pick up station positioned to sequentially receive said liquid containing vessels conveyed by said vessel conveying means, a sample taking probe having one end insertable into that one of said liquid containing vessels being conveyed by said vessel conveying means which is located at said liquid pick up station for removing a sample of liquid from said one of a plurality of liquid containing vessels;

supplemental vessel conveying means supported in superimposed position by said vessel conveying means for conveying a vessel having an emergency or standard sample therein to said sample taking probe, said supplemental vessel conveying means having one position for holding a vessel conveyed by said supplemental conveying means at said liquid pick up station so that the predetermined sequence of conveying said liquid containing vessels by said vessel conveying means is interrupted so that said one end of said sample taking probe is insertable into said vessel conveyed by said supplemental conveying means instead of into said one of a plurality of liquid containing vessels conveyed by said conveying means, and at least one other position for holding a vessel conveyed by said supplemental vessel conveying means away from said liquid pick up station;

means for moving said supplemental vessel conveying means between said one position and said at least one other position;

said one end of said probe being in essentially the same horizontal location when removing a sample from a vessel conveyed by said supplemental vessel conveying means as when removing a sample from a liquid containing vessel conveyed by said vessel conveying means;

said supplemental means comprising a member for holding said sample holding vessel and a sprocket ring, said member being operatively mounted in an eccentric manner with respect to said sprocket ring so as to be rotatable between a first position wherein said member is at said liquid pick up station and a second position wherein said member is kept away from the pick up station.

3. A liquid transfer apparatus for use in an automatic analyzer comprising:

vessel conveying means for successively conveying a plurality of liquid containing vessels for routine analysis to a liquid pick up station of a liquid distributor in a predetermined sequence;

a liquid distributor having said liquid pick up station positioned to sequentially receive said liquid containing vessels conveyed by said vessel conveying means, a sample taking probe having one end insertable into that one of said liquid containing vessels being conveyed by said vessel conveying means which is located at said liquid pick up station for removing a sample of liquid from said one of a plurality of liquid containing vessels;

supplemental vessel conveying means supported in superimposed position by said vessel conveying means for conveying a vessel having an emergency or standard sample therein to said sample taking probe, said supplemental vessel conveying means having one position for holding a vessel conveyed by said supplemental conveying means at said liquid pick up station so that the predetermined sequence of conveying said liquid containing vessels by said vessel conveying means is interrupted so that said one end of said sample taking probe is insertable into said vessel conveyed by said supplemental conveying means instead of into said one of a plurality of liquid containing vessels conveyed by said conveying means, and at least one other position for holding a vessel conveyed by said supplemental vessel conveying means away from said liquid pick up station;

means for moving said supplemental vessel conveying means between said one position and said at least one other position;

said one end of said probe being in essentially the same horizontal location when removing a sample from a vessel conveyed by said supplemental vessel conveying means as when removing a sample from a liquid containing vessel conveyed by said vessel conveying means;

said supplemental means comprising a sprocket ring and means for holding said sample holding vessel which is rotatably and coaxially mounted with said sprocket ring and further including a through-hole and a holding portion for holding the sample holding vessel, said through-hole and said holding portion each being controllably and selectively movable into alignment with said liquid pick up station upon rotation of said holding means.

4. A liquid transfer apparatus for use in an automatic analyzer comprising:

vessel conveying means for successively conveying a plurality of liquid containing vessels for routine analysis to a liquid pick up station of a liquid distributor in a predetermined sequence;

a liquid distributor having said liquid pick up station positioned to sequentially receive a plurality of liquid containing vessels conveyed by said vessel conveying means, a sample taking probe having one end insertable into that one of a plurality of liquid containing vessels being conveyed by said vessel conveying means which is located at said liquid pick up station for removing a sample of liquid from that one of a plurality of liquid containing vessels;

supplemental vessel conveying means supported in superimposed position by said vessel conveying means for conveying a vessel having an emergency or standard sample therein to said sample taking probe, said supplemental vessel conveying means having one position for holding a vessel conveyed by said supplemental conveying means at said liquid pick up station so that the predetermined sequence of conveying a plurality of liquid containing vessels by said vessel conveying means is interrupted so that said one end of said sample taking probe is insertable into a vessel conveyed by said supplemental conveying means instead of into one of a plurality of liquid containing vessels conveyed by said conveying means, and at least one other position for holding a vessel conveyed by said supplemental vessel conveying means away from said liquid pick up station;

means for moving said supplemental vessel conveying means between said one position and said at least one other position in response to a control signal;

means for generating said control signal;

said one end of said probe being in essentially the same horizontal location when removing a sample from a vessel conveyed by said supplemental vessel conveying means as when removing a sample from a liquid containing vesel conveyed by said vessel conveying means;

said supplemental vessel conveying means including a mechanism for indexing and holding said sample holding vessel at said liquid pick up station for a period which permits said probe to remove said sample of liquid therefrom, said mechanism being disposed adjacent said liquid distributor and being responsive to said control signal which is activated whenever an emergency analysis is required.

5. A liquid transfer apparatus according to claim 4 in which the mechanism comprises a base having a through-hole at said liquid pick up station and a rack located on said base and movable in relation to said base between a position adjacent said through-hole and a position away from said through-hole, said position adjacent said through-hole being arranged to place a sample holding vessel carried by said rack at the position of said through-hole;

said one end of said probe being movable through said through-hole into a liquid containing vessel conveyed by said vessel conveying means to said pick up station when said rack is located in said position away from said through-hole.

6. A liquid transfer apparatus according to claim 4 in which the mechanism comprises a base having a through-hole at said liquid pick up station and a rack located on said base and rotatably mounted in relation to said base, said rack being selectively rotatable between a position adjacent said through-hole and a position away from said through-hole to selectively position a sample holding vessel carried by said rack at the position of said through-hole and at another position remote from said position of the through-hole, respectively;

said one end of said probe being movable through said through-hole into a liquid containing vessel conveyed by said vessel conveying means to said pick up station when said rack is located away from said through-hole and being movable into a sample holding vessel carried by said rack when said rack is located adjacent said through-hole.

7. A liquid transfer apparatus according to claim 4 in which the mechanism comprises a base having a first through-hole at said liquid pickup station and a rotary holding body of the turnable type which is mounted on and rotatable relative to said base and on which there are provided a second through-hole and a third through-hole both of which are selectively positionable in alignment with said first through-hole upon rotation of said body;

said second through-hole having a portion for holding a sample holding vessel;

said one end of said probe being movable through said first through-hole and said third through-hole into a liquid containing vessel conveyed by said vessel conveying means to said pick up station, when said third through-hole is aligned with said first through-hole;

said one end of said probe being insertable into a sample holding vessel held in said second through-hole when the latter is aligned with said first through-hole.

8. A liquid transfer apparatus for use in an automatic analyzer comprising:

vessel conveying means for successively conveying a plurality of liquid containing vessels for routine analysis to a liquid pick up station of a liquid distributor in a predetermined sequence;

a liquid distributor having said liquid pick up station positioned to sequentially receive a plurality of liquid containing vessels conveyed by said vessel conveying means, a sample taking probe having one end insertable into that one of the plurality of liquid containing vessels being conveyed by said vessel conveying means which is located at said liquid pick up station for removing a sample of liquid from that one of a plurality of liquid containing vessels;

supplemental vessel conveying means supported in superimposed position by said vessel conveying means for conveying a vessel having an emergency or standard sample therein to said sample taking probe, said supplemental vessel conveying means having one position for holding a vessel conveyed by said supplemental conveying means at said liquid pick up station so that the predetermined sequence of conveying said liquid containing vessels by said vessel conveying means is interrupted so that said one end of said sample taking probe is insertable into a vessel conveyed by said supplemental conveying means instead of into that one of a plurality of liquid containing vessels conveyed by said conveying means which is located at said liquid pick up station, and at least one other position for holding a vessel conveyed by said supplemental vessel conveying means away from said liquid pick up station;

means for moving said supplemental vessel conveying means between said one position and said at least one other position in response to an operator initiated control signal;

means for generating said operator initiated control signal;

said one end of said probe being in essentially the same horizontal location when removing a sample from a vessel conveyed by said supplemental vessel conveying means as when removing a sample from a liquid containing vessel conveyed by said vessel conveying means.

9. A liquid transfer apparatus according to claim 8 in which said vessel conveying means includes a snake chain and is constructed so as to intermittently move said snake chain by means of the drive force of a motor, said snake chain including means for mounting a plurality of liquid containing vessels on said snake chain with equal spacing between such liquid vessels.

10. A liquid transfer apparatus as in claim 8 wherein said vessel conveying means further includes a snake chain and a sprocket ring for driving said snake chain, and said supplemental vessel conveying means comprises a member for holding a sample holding vessel, said member being operatively mounted in an eccentric manner with respect to said sprocket ring so as to be rotatable between said one position wherein said member is at said liquid pick up station and said at least one other position wherein said member is kept away from said liquid pick up station.

11. A liquid transfer apparatus as in claim 8 wherein said vessel conveying means includes a snake chain and a sprocket ring for driving said snake chain, said snake chain being arranged to support a plurality of liquid containing vessels; and wherein said supplemental conveying means comprises means for holding a sample holding vessel, said holding means being rotatably and coaxially mounted with said sprocket ring and including a through-hole and a holding portion for holding a sample holding vessel, said through-hole and said holding portion each being controllably and selectively movable into alignment with said one position for holding a vessel conveyed by said supplemental conveying means at said liquid pick up station upon rotation of said holding means.

12. A liquid transfer apparatus as in claim 8 wherein said supplemental vessel conveying means includes a mechanism for indexing and holding a sample holding vessel at said liquid pick up station for a period which permits said probe to remove a sample liquid therefrom, said mechanism being disposed above said vessel conveying means.

13. A liquid transfer apparatus according to claim 12 in which the mechanism for holding a sample holding vessel comprises a base having a through-hole at said liquid pick up station and a rack located on said base and movable in relation to said base to place a sample holding vessel held thereby at the position of said through-hole;
    said one end of said probe being movable through said through-hole into a liquid vessel conveyed by said vessel conveying means when said rack is located away from said through-hole.

14. A liquid transfer apparatus according to claim 12 in which the mechanism for holding a sample holding vessel comprises a base having a through-hole at said liquid pick up station and a rack located on said base and rotatably mounted in relation to said base, said base holding a sample holding vessel so that such a sample holding vessel is selectively positionable at the position of said through-hold and at another position remote from said position of the through-hole;
    said one end of said probe being movable through said through-hole into a liquid vessel conveyed by said vessel conveying means when said rack is located away from said through-hole.

15. A liquid transfer apparatus according to claim 12 in which the mechanism for holding a sample holding vessel comprises a base having a first through-hole at said liquid pick up station and a rotary holding body of the turnable type which is rotatable relative to said base and on which there are provided a second through-hole and a third through-hole, both of which are selectively positionable in alignment with said first through-hole upon rotation of said body;
    said second through-hole having a portion for holding a sample holding vessel;
    said one end of said probe being movable through said first through-hole and said third through-hole, when said third through-hole is aligned with the first through-hole, into a liquid vessel conveyed by said vessel conveying means;
    said one end of said probe being insertable into a sample holding vessel held in said second through-hole when the latter is aligned with said first through-hole.

* * * * *